United States Patent [19]

Knopf et al.

[11] Patent Number: 5,322,776
[45] Date of Patent: Jun. 21, 1994

[54] DNA SEQUENCES ENCODING PHOSPHOLIPASE $A_2$ ENZYME AND PROCESSES FOR PRODUCING ENZYME

[75] Inventors: John L. Knopf; James Clark, both of Acton, Mass.

[73] Assignee: Genetics Institute, Inc., Cambridge, Mass.

[21] Appl. No.: 4,156

[22] Filed: Jan. 13, 1993

Related U.S. Application Data

[62] Division of Ser. No. 486,628, Feb. 28, 1990.

[51] Int. Cl.$^5$ .............. C12P 21/06; C12N 9/00; C07H 17/00
[52] U.S. Cl. ................ 435/69.1; 435/240.2; 435/320.1; 435/185; 536/23.1; 536/23.2; 536/23.4; 536/23.5
[58] Field of Search ............. 435/69.1, 69.2, 240.1, 435/240.2, 320.1, 183; 536/27, 23.1, 23.2, 23.4, 23.5; 514/169, 182, 237.8, 255, 351, 352; 544/154, 380; 546/300, 304

[56] References Cited

FOREIGN PATENT DOCUMENTS

WO89/05851 6/1989 PCT Int'l Appl. .

OTHER PUBLICATIONS

Leslie et al. (1988) Biochimica et Biophysica Acta:963: pp. 476–492.
E. A. Dennis, Drug Devel. Res., 10:205–220 (1987).
J. Chang et al, Biochem. Pharmacol., 36:2429–2436 (1987).
C. C. Leslie et al, Biochem. Biophys. Acta., 963:476–492 (1988).
J. J. Seilhumer et al, J. Biol. Chem., 264:5335–5338 (1989).
R. M. Kra,er et al, J. Biol. Chem., 264:5768–5775 (1989).
A. Kanda et al, Biochem. Biophys. Res. Comm., 163:42–48 (1989).
Y. Emori et al, J. Biol. Chem., 264(36):21885–21890 (1989).
S. Wasserman, Hospital Practice, pp. 49–58 (1988).
W. Smith, Biochem. J., 259:315–324 (1989).
B. Samuelsson et al, Science, 237:1171–1176 (1987).
S. Moncada et al, "Chapter 28, Prostaglandins, Prostacyclin, Thromboxane $A_2$, and Leukotrienes" pp. 660–673.

*Primary Examiner*—Robert J. Hill, Jr.
*Assistant Examiner*—Gian P. Wang
*Attorney, Agent, or Firm*—Patricia A. McDaniels; Mary Bak; Bruce M. Eisen

[57] ABSTRACT

The invention provides novel DNA and peptide sequences encoding a family of phospholipase $A_2$ enzymes, with specific activities of approximately 20 μmol/min/mg in the mixed micelle assay. These enzymes are useful in methods for detecting the anti-inflammatory potential of various chemical agents. The invention also details novel methods for determining such potential using the novel sequences, methods for making the novel peptides, and methods for developing new anti-inflammatory drugs.

11 Claims, No Drawings

DNA SEQUENCES ENCODING PHOSPHOLIPASE A₂ ENZYME AND PROCESSES FOR PRODUCING ENZYME

This is a division application of U.S. patent application Ser. No. 486,628 filed Feb. 28, 1990.

The present invention relates to novel DNA and peptide sequences encoding a family of phospholipase A₂ enzymes, which are useful in methods for detecting the anti-inflammatory potential of various chemical agents. The invention also details methods for making the novel peptides, and methods for developing new anti-inflammatory drugs.

BACKGROUND OF THE INVENTION

Leukotrienes and prostaglandins are important mediators of inflammation. Leukotrienes recruit inflammatory cells such as neutrophils to an inflamed site, promote the extravasation of these cells and stimulate release of superoxide and proteases which damage the tissue. Leukotrienes also play a pathophysiological role in the hypersensitivity experienced by asthmatics [See, e.g. B. Samuelson et al., *Science*, 237:1171-76 (1987)]. Prostaglandins enhance inflammation by increasing blood flow and therefore infiltration of leukocytes to inflamed sites. Prostaglandins also potentiate the pain response induced by stimuli. prostaglandins and leukotrienes are unstable and are not stored in cells, but are instead synthesized [W. L. Smith, *Biochem. J.*, 259:315-324 (1989) from arachidonic acid in response to stimuli. Likewise arachidonic acid is not free in cells but is released from the sn-2 position of membrane phospholipids by Phospholipase A2 (hereinafter PLA₂). The reaction catalyzed by PLA₂ is believed to represent the rate-limiting step in the process of lipid mediator biosynthesis. When the phospholipid substrate of PLA₂ is of the phosphatidyl choline class with an ether linkage in the sn-1 position, the lysophospholipid produced is the immediate precursor of platelet activating factor (hereafter called PAF), another potent mediator of inflammation [S. I. Wasserman, Hospital practice, 15:49-58 (1988)]. Consequently the direct inhibition of the activity of PLA₂ has been suggested as a useful mechanism for a therapeutic agent, i.e., to interfere with the inflammatory response. [See, e.g., J. Chang et al, *Biochem. Pharmacol.*, 36:2429-2436 (1987)].

A family of PLA₂ enzymes characterized by the presence of a secretion signal sequenced and ultimately secreted from the cell have been sequenced and structurally defined. These secreted PLA₂'s are approximately 14 kD molecular weight and contain seven disulfide bonds which are necessary for activity. These PLA₂s are found in large quantities in mammalian pancreas, bee venom, and various snake venom. [See, e.g., references 13-15 in Chang et al, cited above; and E. A. Dennis, *Drug Devel. Res.*, 10:205-220 (1987).]However, the pancreatic enzyme is believed to serve a digestive function and, as such, should not be important in the production of the inflammatory mediators whose production must be tightly regulated.

Recently, the primary structure of the first human non-pancreatic PLA₂ has been determined. This non-pancreatic PLA₂ is found in platelets, synovial fluid, and spleen and is also a secreted enzyme. This enzyme is a member of the aforementioned family. [See, J. J. Seilhamer et al, *J. Biol. Chem.*, 264:5335-5338 (1989); R. M. Kramer et al, *J. Biol. Chem.*, 264:5768-5775 (1989); and A. Kando et al, *Biochem. Biophys. Res. Comm.*, 163:42-48 (1989)].

However, it is doubtful that this enzyme is important in the synthesis of prostaglandins, leukotrienes and PAF, since the non-pancreatic PLA₂ is an extracellular protein which would be difficult to regulate, and the next enzymes in the biosynthetic pathways for these compounds are intracellular proteins. Moreover, there is evidence that PLA₂ is regulated by protein kinase C and G proteins [R. Burch and J. Axelrod, *Proc. Natl. Acad. Sci. U.S.A.*, 84:6374-6378 (1989)] which are cytosolic proteins which must act on intracellular proteins. It would be impossible for the non-pancreatic PLA2 to function in the cytosol, since the high reduction potential would reduce the disulfide bonds and inactivate the enzyme.

A murine PLA₂ has recently been identified in the murine macrophage cell line, designated RAW 264.7. A specific activity of 2 $\mu$mols/min/mg, resistant to reducing conditions, was reported to be associated with the approximately 60 kD molecule. However, this protein was not purified to homogeneity. [See, C. C. Leslie et al, *Biochem. Biophys. Acta.*, 963:476-492 (1988)]. The references cited above are incorporated by reference herein for information pertaining to the function of the phospholipase enzymes, particularly PLA₂.

There remains a need in the art for a definitive identification of an intracellular PLA₂ enzyme, purified from its natural source or otherwise produced in purified form, which functions intracellularly to produce arachidonic acid in response to inflammatory stimuli. Such enzymes may be useful in methods for developing effective anti-inflammatory agents for therapeutic use in a variety of disease states.

BRIEF SUMMARY OF THE INVENTION

In one aspect the present invention provides a first well-defined intracellular and biologically active mammalian PLA₂ enzyme which is substantially free from association with other mammalian proteins. A novel human biologically active enzyme is characterized by containing all or a portion of the same or substantially the same amino acid sequence reported below in Table I. Alternatively, DNA sequences capable of hybridizing to the sequence of Table I may encode the enzyme.

In another aspect, there is disclosed a second novel mammalian biologically active PLA₂ enzyme characterized by containing all or a portion of the same or substantially the same amino acid sequence reported below in Table II. The partial DNA sequence encoding this novel enzyme is reported in Table II. Alternatively, DNA sequences capable of hybridizing to the sequence of Table II may encode the enzyme.

The mammalian PLA₂ enzymes of this invention are further characterized by each having an apparent molecular weight of approximately 110 kD as determined by sodium dodecyl sulfate polyacrylamide gel electrophoresis under reducing conditions. These enzymes are further characterized by resistance to dithiothreitol, indicating that little to no disulfide bonds exist in the structures of the active homogenous enzymes.

The PLA₂ enzymes of this invention have displayed enzymatic activity in the mixed micelle assay, with a specific activity of 20 $\mu$mols/min/mg associated with the 110 kD protein. This activity is not affected by incubation with disulfide reducing agents. The activity indicates the function of the homogenous enzymes of this invention as cytosolic phospholipase enzymes, involved in regulating the prostaglandin and leukotriene pathways, as well as the biosynthesis of platelet activating factor (PAF).

Another aspect of the invention includes novel DNA sequence coding on expression for a mammalian $PLA_2$ enzyme. The enzyme may be encoded by the DNA sequence reported in Table I, a fragment thereof or a sequence capable of hybridizing thereto. The enzyme may be encoded by the DNA sequence reported in Table II, a fragment thereof or a sequence capable of hybridizing thereto.

Also provided by the present invention are vectors containing a DNA sequence encoding a mammalian $PLA_2$ enzyme in operative association with an expression control sequence. Host cells transformed with such vectors for use in producing recombinant $PLA_2$ are also provided by the present invention.

The vectors and transformed cells of the invention are employed in another aspect, a novel process for producing recombinant mammalian $PLA_2$ enzyme. In this process a cell line transformed with a DNA sequence encoding on expression for $PLA_2$ enzyme in operative association with an expression control sequence therefore is cultured. This claimed process may employ a number of known cells as host cells for expression of the polypeptide. Presently preferred cell lines are mammalian cell lines, insect cells and bacterial cells.

Another aspect of this invention provides methods for identifying anti-inflammatory compounds by determining if a selected compound is capable of inhibiting the action of $PLA_2$ in cleaving a phospholipid to release fatty acids in a mixed micelle assay, a liposome assay, a system utilizing natural membranes, or in whole cells overexpressing this enzyme. A compound capable of inhibiting this $PLA_2$ activity is indicative of use as an anti-inflammatory compound.

Still another aspect of this invention is an anti-inflammatory compound first identified by the method described above as inhibiting the activity of $PLA_2$ of this invention. Novel pharmaceutical compositions may contain a therapeutically effective amount of a compound identified by a method of this invention. These pharmaceutical compositions may be employed in methods for treating disease states or disorders mediated by metabolites of arachidonic acid or PAF, e.g., asthma, rheumatoid arthritis and the like.

A further aspect of the invention, therefore, is a method for treating disorders, diseases, tissue injuries and diseases characterized by an inflammatory reaction by administering to a patient a therapeutically effective amount of a compound first identified by the method of the present invention in a suitable pharmaceutical carrier.

Still another aspect of the present invention are antibodies directed against the $PLA_2$ enzymes of this invention. Anti-$PLA_2$ antibodies may be employed as diagnostic or research agents for use in further exploring and possibly treating inflammatory responses.

Other aspects and advantages of the present invention will be apparent upon consideration of the following detailed description of preferred embodiments thereof.

DETAILED DESCRIPTION OF THE INVENTION

The present invention provides novel biologically active mammalian $PLA_2$ enzymes, substantially free of association with other mammalian proteinaceous materials. These proteins may be produced in a variety of ways, including via recombinant DNA techniques to enable large scale production of pure, active $PLA_2$ useful for screening compounds for anti-inflammatory therapeutic applications, and developing antibodies for therapeutic, diagnostic and research use.

Human $PLA_2$ was originally purified from the human monocytic cell line U937, available from the American Type Culture Collection, 12301 Parklawn Drive, Rockville, Md. (ATCC) under accession number ATCC CRL 1593. The U937 cell line was chosen due to its high levels of $PLA_2$ activity, even in the presence of disulfide reducing agents. However, $PLA_2$ may also be produced by other human cell lines.

The purification procedure is described in detail in Example 1 below. Briefly described, cells were disrupted by $N_2$ cavitation in a pH 7.5 iso-osmotic lysis buffer containing dithiothreitol (DTT), ethylenediaminetetraacetic acid (EDTA) and protease inhibitors. The 100,000× g supernatant was purified by elution through the following order of chromatographic columns: phenyl, heparin, hydroxyapatite, size exclusion and anion exchange chromatography. DTT, a disulfide reducing agent, was added to the elution buffers to inactivate any low molecular weight $PLA_2$s. In this manner, selection was directed to purification of cytosolic $PLA_2$.

At this point of the purification, the human $PLA_2$ enzyme preparation is characterized by a specific activity of approximately 4 μmols/min/mg in the mixed micelle assay described in Example 3, below. This specific activity is comparable to that reported for the intracellular murine $PLA_2$ by Leslie et al, cited above.

However, when the purified protein was analyzed by SDS-PAGE under reducing conditions, two major proteins were observed with apparent molecular weights of approximately 60 kD and 110 kD. The smaller protein was approximately 4-fold more abundant. Further purification on a size exclusion column separated the two proteins, with the activity remaining associated with the 110 kD protein. No activity was associated with the 60 kD protein.

The specific activity of the pure homogeneous material is estimated to be approximately 20 μmols/min/mg using the mixed micelle assay described in Example 3 to measure activity, and the intensity of the 110 kD band on a silver stained SDS-PAGE gel to quantitate protein.

The 110 kD protein was run on a SDS-PAGE gel, the region of the gel corresponding to 110 kD was excised and subjected to digestion by trypsin. The tryptic fragments were separated by C-8 reverse phase chromatography and the amino acid sequences were determined for several fragments. Degenerate oligonucleotides encoding two of these fragments were used to screen a cDNA library prepared from the U937 cell line, as described in Example 5.

One complete clone was sequenced. The $PLA_2$ cDNA sequence from this clone is shown in Table I below. The DNA sequence of Table I contains approximately 2247 nucleotides in the proper reading frame to encode a protein having a calculated molecular weight of approximately 85 kD.

Human $PLA_2$ according to this invention is characterized by the same or substantially the same approximately 749 predicted amino acid protein sequence (single letter code) encoded by that DNA sequence, as illustrated in Table I below. All tryptic fragments that were sequenced are present in the $PLA_2$ cDNA sequence and identified by underlining. Those tryptic fragments indicated by asterisks in the Table were used to design the oligonucleotides. Fragments of the sequence reported in Table I may also retain PLA$_2$ biological activity.

The cDNA sequence of Table I encodes biologically active human PLA$_2$, based on detection of the functional polypeptides produced by mammalian cells. The active, recombinantly derived human PLA$_2$ migrates as an approximately 110 kD protein on SDS-PAGE, as does the purified enzyme. The cloned sequence of Table I in plasmid PMT-PLA$_2$ was deposited with the American Type Culture Collection, 12301 Parklawn Drive, Rockville, Md. on Feb. 27, 1990 under ATCC Accession No. 40759.

TABLE I

| | | | | | | | | | | | |
|---|---|---|---|---|---|---|---|---|---|---|---|
| ATG | TCA | TTT | ATA | GAT | CCT | TAC | CAG | CAC | ATT | ATA | GTG | GAG |
| M | S | F | I | D | P | Y | Q | H | I | I | V | E |
| CAC | CAG | TAT | TCC | CAC | AAG | TTT | ACG | GTA | GTG | GTG | TTA | CGT |
| H | Q | Y | S | H | K | F | T | V | V | V | L | R |
| GCC | ACC | AAA | GTG | ACA | AAG | GGG | GCC | TTT | GGT | GAC | ATG | CTT |
| A | T | K | V | T | K | G | A | F | G | D | M | L |
| GAT | ACT | CCA | GAT | CCC | TAT | GTG | GAA | CTT | TTT | ATC | TCT | ACA |
| D | T | P | D | P | Y | V | E | L | F | I | S | T |
| ACC | CCT | GAC | AGC | AGG | AAG | AGA | ACA | AGA | CAT | TTC | AAT | AAT |
| T | P | D | S | R | K | R | T | R | H | F | N | N |
| GAC | ATA | AAC | CCT | GTG | TGG | AAT | GAG | ACC | TTT | GAA | TTT | ATT |
| D | I | N | P | V | W | N | E | T | F | E | F | I |
| TTG | GAT | CCT | AAT | CAG | GAA | AAT | GTT | TTG | GAG | ATT | ACG | TTA |
| L | D | P | N | Q | E | N | V | L | E | I | T | L |
| ATG | GAT | GCC | AAT | TAT | GTC | ATG | GAT | GAA | ACT | CTA | GGG | ACA |
| M | D | A | N | Y | V | M | K | E | T | L | G | T |
| GCA | ACA | TTT | ACT | GTA | TCT | TCT | ATG | AAG | GTG | GGA | GAA | AAG |
| A | T | F | T | V | S | S | M | K | V | G | E | K |
| AAA | GAA | GTT | CCT | TTT | ATT | TTC | AAC | CAA | GTC | ACT | GAA | ATG |
| K | E | V | P | F | I | F | N | Q | V | T | E | M |
| GTT | CTA | GAA | ATG | TCT | CTT | GAA | GTT | TGC | TCA | TGC | CCA | GAC |
| V | L | E | M | S | L | E | V | C | S | C | P | D |
| CTA | CGA | TTT | AGT | ATG | GCT | CTG | TGT | GAT | CAG | GAG | AAG | ACT |
| L | R | F | S | M | A | L | C | D | Q | E | K | T |
| TTC | AGA | CAA | CAG | AGA | AAA | GAA | CAC | ATA | AGG | GAG | AGC | ATG |
| F | R | Q | Q | R | K | E | H | I | R | E | S | M |
| AAG | AAA | CTC | TTG | GGT | CCA | AAG | AAT | AGT | GAA | GGA | TTG | CAT |
| K | K | L | L | G | P | K | N | S | E | G | L | H |
| TCT | GCA | CGT | GAT | GTG | CCT | GTG | GTA | GCC | ATA | TTG | GGT | TCA |
| S | A | R | D | V | P | V | V | A | I | L | G | S |
| GGT | GGG | GGT | TTC | CGA | GCC | ATG | GTG | GGA | TTC | TCT | GGT | GTG |
| G | G | G | F | R | A | M | V | G | F | S | G | V |
| ATG | AAG | GCA | TTA | TAC | GAA | TCA | GGA | ATT | CTG | GAT | TGT | GCT |
| M | K | A | L | Y | E | S | G | I | L | D | C | A |
| ACC | TAC | GTT | GCT | GGT | CTT | TCT | GGC | TCC | ACC | TGG | TAT | ATG |
| T | Y | V | A | G | L | S | G | S | T | W | Y | M |
| TCA | ACC | TTG | TAT | TCT | CAC | CCT | GAT | TTT | CCA | GAG | AAA | GGG |
| S | T | L | Y | S | H | P | D | F | P | E | K | G |
| CCA | GAG | GAG | ATT | AAT | GAA | GAA | CTA | ATG | AAA | AAT | GTT | AGC |
| P | E | E | I | N | E | E | L | M | K | N | V | S |
| CAC | AAT | CCC | CTT | TTA | CTT | CTC | ACA | CCA | CAG | AAA | GTT | AAA |
| H | N | P | L | L | L | L | T | P | Q | K | V | K |
| AGA | TAT | GTT | GAG | TCT | TTA | TGG | AAG | AAG | AAA | AGC | TCT | GGA |
| R | Y | V | E | S | L | W | K | K | K | S | S | G |
| CAA | CCT | GTC | ACC | TTT | ACT | GAT | ATC | TTT | GGG | ATG | TTA | ATA |
| Q | P | V | T | F | T | D | I | F | G | M | L | I |
| GGA | GAA | ACA | CTA | ATT | CAT | AAT | AGA | ATG | AAT | ACT | ACT | CTG |
| G | E | T | L | I | H | N | R | M | N | T | T | L |

TABLE I-continued

```
AGC AGT TTG AAG GAA AAA GTT AAT ACT GCA CAA TGC CCT
 S   S   L   K   E   K   V   N   T   A   Q   C   P

TTA CCT CTT TTC ACC TGT CTT CAT GTC AAA CCT GAC GTT
 L   P   L   F   T   C   L   H   V   K   P   D   V

TCA GAG CTG ATG TTT GCA GAT TGG GTT GAA TTT AGT CCA
 S   E   L   M   F   A   D   W   V   E   F   S   P

TAC GAA ATT GGC ATG GCT AAA TAT GGT ACT TTT ATG GCT
 Y   E   I   G   M   A   K   Y   G   T   F   M   A

CCC GAC TTA TTT GGA AGC AAA TTT TTT ATG GGA ACA GTC
 P   D   L   F   G   S   K   F   F   M   G   T   V

GTT AAG AAG TAT GAA GAA AAC CCC TTG CAT TTC TTA ATG
 V   K   K   Y   E   E   N   P   L   H   F   L   M

GGT GTC TGG GGC AGT GCC TTT TCC ATA TTG TTC AAC AGA
 G   V   W   G   S   A   F   S   I   L   F   N   R

GTT TTG GGC GTT TCT GGT TCA CAA AGC AGA GGC TCC ACA
 V   L   G   V   S   G   S   Q   S   R  *G   S   T

ATG GAG GAA GAA TTA GAA AAT ATT ACC ACA AAG CAT ATT
 M   E   E   E   L   E   N   I   T   T   K*  H   I

GTG AGT AAT GAT AGC TCG GAC AGT GAT GAT GAA TCA CAC
 V   S   N   D   S   S   D   S   D   D   E   S   H

GAA CCC AAA GGC ACT GAA AAT GAA GAT GCT GGA AGT GAC
 E   P   K   G   T   E   N   E   D   A   G   S   D

TAT CAA AGT GAT AAT CAA GCA AGT TGG ATT CAT CGT ATG
 Y   Q   S   D   N   Q   A   S   W   I   H   R   M

ATA ATG GCC TTG GTG AGT GAT TCA GCT TTA TTC AAT ACC
 I   M   A   L   V   S   D   S   A   L   F   N   T

AGA GAA GGA CGT GCT GGG AAG GTA CAC AAC TTC ATG CTG
 R   E   G   R   A   G   K   V   H   N   F   M   L

GGC TTG AAT CTC AAT ACA TCT TAT CCA CTG TCT CCT TTG
 G   L   N   L   N   T   S   Y   P   L   S   P   L

AGT GAC TTT GCC ACA CAG GAC TCC TTT GAT GAT GAT GAA
 S   D   F   A   T   Q   D   S   F   D   D   D   E

CTG GAT GCA GCT GTA GCA GAT CCT GAT GAA TTT GAG CGA
 L   D   A   A   V   A   D   P   D   E   F   E   R

ATA TAT GAG CCT CTG GAT GTC AAA AGT AAA AAG ATT CAT
 I   Y   E   P   L   D   V   K   S   K   K   I   H

GTA GTG GAC AGT GGG CTC ACA TTT AAC CTG CCG TAT CCC
 V   V   D   S   G   L   T   F   N   L   P   Y   P

TTG ATA CTG AGA CCT CAG AGA GGG GTT GAT CTC ATA ATC
 L   I   L   R   P   Q   R   G   V   D   L   I   I

TCC TTT GAC TTT TCT GCA AGG CCA AGT GAC TCT AGT CCT
 S   F   D   F   S   A   R   P   S   D   S   S   P

CCG TTC AAG GAA CTT CTA CTT GCA GAA AAG TGG GCT AAA
 P   F   K   E   L   L   L   A   E   K   W   A   K

ATG AAC AAG CTC CCC TTT CCA AAG ATT GAT CCT TAT GTG
 M   N   K   L   P   F   P   K   I   D   P   Y   V

TTT GAT CGG GAA GGG CTG AAG GAG TGC TAT GTC TTT AAA
 F   D   R   E   G   L   K   E   C   Y   V   F   K

CCC AAG AAT CCT GAT ATG GAG AAA GAT TGC CCA ACC ATC
 P   K   N   P   D   M   E   K   D   C   P   T   I

ATC CAC TTT GTT CTG GCC AAC ATC AAC TTC AGA AAG TAC
 I   H   F   V   L   A   N   I   N   F   R  *K   Y

AAG GCT CCA GGT GTT CCA AGG GAA ACT GAG GAA GAG AAA
 K   A   P   G   V   P*  R   E   T   E   E   E   K
```

TABLE I-continued

| | | | | | | | | | | | |
|---|---|---|---|---|---|---|---|---|---|---|---|
| GAA | ATC | GCT | GAC | TTT | GAT | ATT | TTT | GAT | GAC | CCA | GAA | TCA |
| E | I | A | D | F | D | I | F | D | D | P | E | S |

| CCA | TTT | TCA | ACC | TTC | AAT | TTT | CAA | TAT | CCA | AAT | CAA | GCA |
|---|---|---|---|---|---|---|---|---|---|---|---|---|
| P | F | S | T | F | N | F | Q | Y | P | N | Q | A |

| TTC | AAA | AGA | CTA | CAT | GAT | CTT | ATG | CAC | TTC | AAT | ACT | CTG |
|---|---|---|---|---|---|---|---|---|---|---|---|---|
| F | K | R | L | H | D | L | M | H | F | N | T | L |

| AAC | AAC | ATT | GAT | GTG | ATA | AAA | GAA | GCC | ATG | GTT | GAA | AGC |
|---|---|---|---|---|---|---|---|---|---|---|---|---|
| N | N | I | D | V | I | K | E | A | M | V | E | S |

| ATT | GAA | TAT | AGA | AGA | CAG | AAT | CCA | TCT | CGT | TGC | TCT | GTT |
|---|---|---|---|---|---|---|---|---|---|---|---|---|
| I | E | Y | R | R | Q | N | P | S | R | C | S | V |

| TCC | CTT | AGT | AAT | GTT | GAG | GCA | AGA | AGA | TTT | TTC | AAC | AAG |
|---|---|---|---|---|---|---|---|---|---|---|---|---|
| S | L | S | N | V | E | A | R | R | F | F | N | K |

| GAG | TTT | CTA | AGT | AAA | CCC | AAA | GCA |
|---|---|---|---|---|---|---|---|
| E | F | L | S | K | P | K | A |

The nucleotide sequence of this human PLA$_2$ cDNA of the invention has been compared with the nucleotide sequences recorded in Genbank. The only factor with which the human PLA$_2$ sequence of Table I is believed to share significant sequence similarity is protein kinase C-gamma (PKC). This sequence similarity may indicate a region of PKC and PLA$_2$ which share a common function. Likely functions include the regulation of the two enzymes by calcium and the calcium dependent binding of these enzymes to membranes.

The second mammalian PLA$_2$ enzyme of this invention was originally purified from the murine monocytic cell line RAW 264.7, available from the ATCC under accession number TIB71. This factor may also be isolated from other murine cell lines. The methods used to isolate and purify the murine PLA$_2$ enzyme are analogous to those described above for the human PLA$_2$ from U937 cells and are described in detail in Example 2.

Like the human PLA$_2$ protein described above, the initially purified protein wa analyzed by SDS-PAGE under reducing conditions and two major proteins were observed having apparent molecular weights of approximately 60 kD and 110 kD. Further purification on a size exclusion column as described for human PLA$_2$ (also as described in Example 2 below) indicated that the 60 kD protein was an inactive contaminant and separated it from the active 110 kD protein. Once again, DTT was used to inactivate any low molecular weight PLA$_2$ enzymes.

The finally purified, homogeneous, approximately 110 kD murine PLA$_2$ enzyme of this invention is characterized by a specific activity of approximately 20 μmols/min/mg in the mixed micelle assay described in Example 3. The intensity of the 110 kD band on a silver stained SDS-PAGE gel was used to quantitate protein. This specific activity is 10-fold higher than that value observed by Leslie et al, cited above, for the 60 kD PLA$_2$ reportedly obtained from the same cell line. Due to the lower degree of purity obtained for the reported smaller molecular weight protein, it is likely that the 60 kD protein characterized as PLA$_2$ by Leslie et al is the contaminant of the 110 kD PLA$_2$ of this invention and, as such, does not possess PLA$_2$ activity.

To obtain production of this murine PLA$_2$ protein by recombinant methods, a sequence from a partial clone of the U937 PLA$_2$ (from base #877 to the 3' end of the sequence of Table I) was used to screen a cDNA library prepared from the RAW 264.7 cell line. One positive clone, which was isolated from a library of 1×10$^6$ clones, was partially sequenced. The partial sequence of the PLA$_2$ cDNA from this clone (clone #7) and the associated predicted amino acid sequence, is shown in Table II below. All or a fragment of this cDNA is believed to encode murine PLA$_2$ of this invention. The sequence determination of this clone is on-going.

The purified RAW 264.7 PLA$_2$ was also digested into tryptic fragments and sequenced as described for the human PLA$_2$ enzyme. The sequence of two tryptic fragments (underlined in the sequence of Table II) were obtained. DNA sequence was available for the first 15 of 18 amino acids of one of the tryptics, and this sequence is underlined in the table. The sequence for the other tryptic disagreed at two amino acids (marked by asterisks) within the deduced sequence. Based on the partial sequence, the RAW 264.7 enzyme is the murine homologue of the human PLA$_2$ of this invention.

Murine PLA$_2$ according to this invention is a protein comprising the same or substantially the same predicted amino acid protein sequence (single letter code) encoded by the partial cDNA sequence illustrated in Table II below as well as additional sequence. The partial sequence or fragments of the sequence reported in Table II may also retain PLA$_2$ biological activity.

TABLE II

| ATG | TCT | TTC | ATA | GAT | CCT | TAT | CAG | CAC | ATT | ATA | GAG | GAA | CAC |
|---|---|---|---|---|---|---|---|---|---|---|---|---|---|
| M | S | F | I | D | P | Y | Q | H | I | I | V | E | H |

| CAG | TNC | TCC | CAT | AAG | TTT | ACT | GTT | TGT | GTT | CTA | CGT | GCC | ACC |
|---|---|---|---|---|---|---|---|---|---|---|---|---|---|
| Q | ? | S | H | K | F | T | V | V | V | L | R | A | T |

| AAA | GTA | ACC | AAG | GGG | ACC | TTT | GGC | GAT | ATG | CTG | GAC | ACT | CCA |
|---|---|---|---|---|---|---|---|---|---|---|---|---|---|
| K | T | V | K | G | T | F | G | D | M | L | D | T | P |

TABLE II-continued

| | | | | |
|---|---|---|---|---|
| GAT | CCT | TAT | GTG | GAA |
| D | P | Y | V | E |

| | | | | | | | | | | |
|---|---|---|---|---|---|---|---|---|---|---|
| ATC | GTG | AGT | AAT | GAC | AGC | TCC | GAC | AGT | GAT | GAT | GAG | GCT | CAA |
| I | V | S | N | D | S | S | D | S | D | D | E | A | Q |

| GGA | CCC | AAA | GGC | ACC | GAG | AAT | GAA | GAA | GCT | GAA | AAA | GAG | TAC |
|---|---|---|---|---|---|---|---|---|---|---|---|---|---|
| G | P | K | G | T | E | N | E | E | A | E | K | E | Y |

| CAA | AGC | GAC | AAC | CAA | GCA | AGT | TGG | GTC | CAT | CGG | ATG | CTA | ATG |
|---|---|---|---|---|---|---|---|---|---|---|---|---|---|
| Q | S | D | N | Q | A | S | W | V | H | R | M | L | M |

| GCC | TTG | GTG | AGC | GAC | TCG | GCT | TTA | TTC | AAT | ACC | CGA | GAA | GGA |
|---|---|---|---|---|---|---|---|---|---|---|---|---|---|
| A | L | V | S | D | S | A | L | F | N | T | R | E | G |

| CGT | GCC | GGA | AAG | GTG | CAT | AAC | TTC | ATG | CTG | GGC | TTG | AAT | CTC |
|---|---|---|---|---|---|---|---|---|---|---|---|---|---|
| R | A | G | K | V | H | N | F | M | L | G | L | N | L |

| AAC | ACA | TGA | TAT | CCA | CTG | TCT | CCC | CTG | AGA | GAC | TTC | AGC | TCT |
|---|---|---|---|---|---|---|---|---|---|---|---|---|---|
| N | T | S | Y | P | L | S | P | L | R | D | F | S | S |

| CAG | GAT | TCC | TTC |
|---|---|---|---|
| Q | D | S | F |

Allelic variations (naturally-occurring base changes in the species population which may or may not result in an amino acid change) of the DNA sequences of Table I or Table II, encoding the PLA$_2$ factors described above are also included in the present invention, as well as fragments, or derivatives thereof. Thus the present invention also encompasses these novel DNA sequences, free of association with DNA sequences encoding other mammalian proteins, and coding on expression for novel mammalian PLA$_2$ polypeptides.

DNA sequences of this invention also include those novel sequences which hybridize under stringent hybridization conditions [see, T. Maniatis et al, *Molecular Cloning (A Laboratory Manual)*, Cold Spring Harbor Laboratory (1982), pages 387 to 389] to the DNA sequence of Table I or Table II. An example of one such stringent hybridization condition is hybridization in 4XSSC at 65° C., followed by a washing in 0.1XSSC at 65° C. for thirty minutes. Alternatively an exemplary stringent hybridization condition is in 50% formamide, 4XSSC at 42° C.

DNA sequences, other than those of the known approximately 14 kD PLA$_2$ enzymes of pancreas or non-pancreatic origin, which hybridize to the sequences of Table I or II for human or murine PLA$_2$ under relaxed hybridization conditions and which code on expression for PLA$_2$ peptides having PLA$_2$ activity in the mixed micelle assay of Example 3, are also included in the present invention. Examples of such non-stringent hybridization conditions are 4XSSC at 50° C. or hybridization with 30–40% formamide at 42° C. For example, a DNA sequence which shares regions of significant homology, with the sequences of human or murine PLA$_2$ of this invention and encodes a protein having one or more PLA$_2$ biological properties clearly encodes a PLA$_2$ enzyme even if such a DNA sequence would not stringently hybridize to the human PLA$_2$ sequence of Table I or the murine PLA$_2$ sequence of Table II.

Similarly, DNA sequences which code for PLA$_2$ enzymes of this invention but which differ in codon sequence due to the degeneracies of the genetic code are also encompassed by this invention. Variations in the DNA sequence of PLA$_2$ which are caused by point mutations or by induced modifications of the sequences of Tables I and II, which enhance the activity, half-life or production of the polypeptides encoded thereby are also encompassed in the invention.

PLA$_2$ polypeptides may also be produced by known conventional chemical synthesis. Methods for constructing the polypeptides of the present invention by synthetic means are known to those of skill in the art. The synthetically-constructed PLA$_2$ polypeptide sequences, by virtue of sharing primary, secondary, or tertiary structural and conformational characteristics with PLA$_2$ polypeptides may possess PLA$_2$ biological properties in common therewith. Thus, they may be employed as biologically active or immunological substitutes for natural, purified PLA$_2$ enzymes in screening of therapeutic compounds and in immunoloqical processes for the development of anti-PLA$_2$ antibodies.

The PLA$_2$ enzymes provided herein also include proteins characterized by amino acid sequences similar to those of purified recombinant PLA$_2$ but into which modifications are naturally provided or deliberately engineered. For example, modifications in the peptide or DNA sequences can be made by one skilled in the art using known techniques. Modifications of interest in the PLA$_2$ sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to one skilled in the art. [See, e.g., U.S. Pat. No. 4,518,584.]

Other fragments and derivatives of the sequences of human or murine PLA$_2$ which would be expected to retain PLA$_2$ activity in whole or in part and may thus be useful for screening or other immunological methodologies may also be easily made by one of skill in the art given the disclosures herein. Such modifications are believed to be encompassed by this invention.

The present invention also provides a method for producing the PLA$_2$ proteins of human or murine origin described in Tables I and II. The method of the present invention involves culturing a suitable cell or cell line, which has been transformed with a DNA sequence coding on expression for a PLA$_2$ polypeptide or an active fragment thereof under the control of known regulatory sequences. Regulatory sequences include promoter fragments, terminator fragments and other suitable sequences which direct the expression of the protein in an appropriate host cell.

Suitable cells or cell lines for use in expressing the PLA$_2$ proteins may be mammalian cells, such as Chinese hamster ovary cells (CHO), RAT2 cells or 3T3 cells. The selection of suitable mammalian host cells and methods for transformation culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Other suitable mammalian cell lines, are the monkey COS-1 cell line, and the CV-1 cell line. Example 7 describes the expression of the human PLA$_2$ protein in a monkey COS-1 cell expression system. Example 10 describes the expression of the human PLA$_2$ protein in CHO cells.

The novel PLA$_2$ proteins of this invention can also be conveniently prepared in invertebrate cells, specifically, in insect cells. One presently preferred method for producing this novel composition employs *Autographa californica* nuclear polyhedrosis virus (AcNPV) as an expression vector. See, e.g., Miller et al, *Genetic Engineering*, 8:277–298 (Plenum Press 1986) and references cited therein; and procedures described in published European patent application 155,476]. Samples of the extensively studied AcNPV may be obtained from numerous sources, including the Yale Arbovirus Research Unit (YARU) located in New Haven, Conn. Other viruses known to those skilled in the art may be similarly employed.

Briefly, a segment of AcNPV DNA encompassing the polyhedrin gene and promoter is cloned in *E. coli* using a plasmid vector. The polyhedrin gene region on the recombinant plasmid DNA is modified by deletion of a portion of the structural gene and insertion of a synthetic polylinker containing a band of restriction endonuclease cleavage sites for convenient insertion into the polyhedrin gene region of the PLA$_2$ DNA segment. The PLA$_2$ DNA attached to a functional polyhedrin promoter and flanked by viral sequences in inserted in a selected enzyme cleavage site of the plasmid DNA, so that it is under the control of the viral polyhedrin promoter. This method substantially preserves that portion of the polyhedrin gene between the start site of transcription and the start site of RNA translation, i.e., the segment of the gene encoding the untranslated portion of the RNA and thus preserves any regulatory signals contained therein.

The plasmid is then co-transfected with wild-type AcNPV viral DNA into suitable insect host cells. Thereafter, either by gene conversion or cell-mediated homologous recombination, the DNA from the recombinant plasmid replaces the polyhedrin gene on the full length wild-type AcNPV chromosome. When RNA synthesis occurs during virus infection, the mRNA read from the inserted exogenous DNA directs the expression of the new PLA$_2$ composition. Specific viruses containing the PLA$_2$ DNA may be selected for passenger DNA-containing viruses by visually screening plaques under the light microscope for absence of polyhedrin inclusion bodies (PIBS). Following plaque purification of the recombinant virus, the desired PLA$_2$ enzyme can be synthesized by cells infected with this recombinant virus. Example 8 describes an insect expression system of interest for recombinant production of these enzymes.

Bacterial cells may also be useful a host cells suitable for the present invention, provided that the molecule produced therein retains activity. For example, the various strains of *E. coli* (e.g., HB101, MC1061) are well-known as host cells in the field of biotechnology. Various strains of *B. subtilis*, Pseudomonas, other bacilli and the like may also be employed in this method. Example 9 describes a bacterial expression system of interest for production of these enzymes.

Many strains of yeast cells known to those skilled in the art are also available as host cells for expression of the polypeptides of the present invention. These yeast vectors are constructed employing yeast regulatory sequences to express the cDNA encoding PLA$_2$ in yeast cells to yield secreted extracellular active PLA$_2$. [See, e.g., procedures described in published PCT application WO 86/00639 and European patent application EP 123,289.]

The present invention also provides vectors for use in the method of expression of novel PLA$_2$ enzymes. These vectors contain the novel PLA$_2$ DNA sequences which code for PLA$_2$ polypeptides of the invention. Vectors incorporating truncated or altered fragments of PLA$_2$, allelic variants thereof, or modified sequences as described above are also embodiments of the present invention and useful in the production of PLA$_2$ polypeptides. The vector employed in the method also contains selected regulatory sequences in operative association with the DNA coding sequences of the invention and capable of directing the replication and expression thereof in selected host cells. The vector used in the examples below is a plasmid designed for expression of heterologous proteins in COS cells. This expression plasmid PMT-PLA$_2$ described in detail in Example 7.

The novel mammalian PLA$_2$ enzymes of this invention, purified to homogeneity from cell sources or produced recombinantly or synthetically, may be used in novel methods for screening compounds for anti-inflammatory activity, as described in Example 11. For example, a selected compound may be employed in the mixed micelle assay of Example 3 with a selected PLA$_2$ enzyme of this invention. If the normal action of the enzyme is inhibited, i.e., the phospholipid is not cleaved to release the inflammatory mediator precursor, e.g., fatty acid, the compound demonstrates potential as an inhibitor of inflammatory reaction.

Similarly the ability of the selected compound may be studied for inhibition of the PLA$_2$ activity in a liposome assay. An assay system utilizing natural membranes may also be designed to assess the anti-inflammatory potential of selected compounds. These assays are further described in Examples 3 and 11 below.

Alternatively a selected compound may be added to whole cells which overexpress the PLA$_2$ and the cells examined for inhibition of cleavage of the sn-2 acyl bond. For example, both normal cells and cells found to overexpress the PLA$_2$ enzyme are cultured in labelled arachidonic acid. Signal is measured between the secreted products of both the normal and overexpressing cells to provide a baseline of PLA$_2$ expression. A selected compound is then added to cultures and the cultures are grown in label arachidonic acid. If there is a difference in the signal (e.g., the amount of arachidonic acid produced) in the cells in the presence of the compound, it inhibited PLA$_2$ activity and may be a potential anti-inflammatory compound.

Other uses for these novel PLA$_2$ enzymes or active fragments thereof are in the development of monoclonal and polyclonal antibodies. Such antibodies may be generated employing PLA$_2$, a fragment thereof, or a modified or allelic version thereof as an antigen. By using standard methods for the development of such antibodies known to one of skill in the art, polyclonal or monoclonal antibodies are made which may be useful as research or diagnostic agents to study PLA$_2$ and inflammatory functions directly.

A pharmaceutical preparation or formulation containing a compound identified by the screening method of the present invention to inhibit the function of PLA$_2$, may be employed to treat, among other conditions, those disease states characterized by inflammatory reactions, e.g., rheumatoid arthritis, psoriasis, asthma, inflammatory bowel disease, and other diseases mediated by prostaglandins, leukotrienes or PAF. Therapeutic treatment with compounds identified by the method of the present invention may avoid undesirable side effects caused by treatment with presently available anti-inflammatory drugs.

Therefore, as another aspect of this invention, methods and compositions are provided for the treatment of inflammatory conditions. Such compositions may comprise a therapeutically effective amount of a PLA$_2$ inhibitor or competitor compound first identified according to the present invention in admixture with an optional pharmaceutically acceptable carrier. Alternatively the therapeutic compound according to this invention may contain an antibody to PLA$_2$ which is capable of binding thereto and rendering the enzyme incapable of acting normally.

Pharmaceutical compositions of this invention can be systematically administered parenterally. Alternatively, the composition may be administered intravenously. If desirable, the composition may be administered subcutaneously. When systematically administered, the therapeutic composition for use in this invention is in the form of a pyrogen-free, parenterally acceptable aqueous solution. The composition may also be made for topical application. The preparation of such pharmaceutically acceptable protein solutions or formulations, having due regard to pH, isotonicity, stability and the like, is within the skill of the art.

The dosage regimen for these compositions involved in a method for treating the above-described conditions will be determined by the attending physician considering various factors which modify the action of drugs, e.g. the type of compound employed, the condition, body weight, sex and diet of the patient, the severity of any infection, time of administration and other clinical factors. Progress of the treated patient can be monitored by conventional methods.

The following examples illustratively describe the cloning, expression and production of human PLA$_2$ and other methods and products of the present invention. These examples ar for illustration only and do not limit the scope of the present invention.

EXAMPLE 1—PURIFICATION OF HUMAN PLA$_2$

The human monocytic cell line U937 [ATCC CRL 1593] was selected as a potential source for human intracellular PLA$_2$. Using a humidified incubator at 37° C. and 5% CO$_2$, approximately $10^{11}$ U937 cells were cultured in RPMI media supplemented with 10% fetal bovine serum, penicillin (100 units/mL), streptomycin (100 μg/mL) and glutamine (20 mM). The cells were harvested by concentration using tangential filtration followed by centrifugation. The pelletted cells were twice washed in ice cold phosphate buffered saline (PBS).

The washed cells were suspended in HEPES (10 mM) lysis buffer at pH7.5 containing sucrose (0.34M), EDTA (1 mM), DTT (0.1 mM), ATP (1 mM), leupeptin (1 μg/mL) and freshly added PMSF (1 mM). The cells were lysed by N$_2$ cavitation at 600–700 psi and the lysate was centrifuged at 50,000 g×60 minutes. PLA$_2$ was purified from the supernatant.

The cleared lysate was adjusted to 0.5M NH$_4$SO$_4$, centrifuged at 50,000 g×60 minutes, filtered through a Millipak 60 filter unit, and loaded onto a Toso Haas phenyl-5 PW column (15 cm×21.5 mm) that was previously equilibrated with 20 mM Tris HCl buffer (pH7.5) containing 5 mM DTT and 0.5M NH$_4$SO$_4$. The PLA$_2$ activity was eluted at 8 mL/minutes with a 250 mL reverse gradient from 0.5 to 0M NH$_4$SO$_4$ with an extended wash at 0M salt. The activity eluting at 0M salt was concentrated 10 fold to approximately 10 mL using an Amicon filtration apparatus with a PM-10 filter; 400 μl (pH6.8) MES buffer (1M), 1 mL glycerol and 50 μL DTT (1M) were added; and the solution was passed through a Heparin Sepharose CL-6B column (1 cm×12 cm) equilibrated with 40 mM MES at pH 6.8 containing glycerol (10%) and DTT (5mM). Potassium phosphate buffer (pH6.8) and CaCl2 were added to the heparin column eluent to final concentrations of 10 mM and 10 μM respectively and the sample was loaded onto a Biogel HPHT column (7.8×100 mm) equilibrated with the same levels of phosphate buffer and CaCl2.

Fractions (1 mL) were eluted by a linear potassium phosphate gradient (10–500 mM) at a flow rate of 0.4 mL/minute. The activity eluted near 140 mM phosphate. The active fractions were concentrated in a Centricon-30 and injected onto a TSK-Gel G3000-SW size exclusion column (60 cm×7.5 mm) which was both equilibrated and run in pH6.5 MES buffer (40 mM) containing KCl (300 mM), DTT (5 mM) and octylglucoside (3 mM). The flow rate was 0.4 mL/minute, and the fraction size was 0.5 mL/minute.

The activity eluted at a molecular weight of approximately 100 kD. This material Was diluted 4 fold with Tris HCl (20 mM) buffer at pH7.5 containing glycerol (10%) and DTT (5 mM), loaded onto a Mono-Q HR 5/5 column equilibrated with the same buffer and eluted with a 60 mL 0-M KCl linear gradient at a flow rate of 1 mL/minute while collecting 1 mL fractions. The PLA$_2$ activity eluted in fractions 38–40 at approximately 400 mM salt.

When fractions 36–42 were analyzed by SDS-PAGE using Biorad silver stain for visualization, two major bands were observed with apparent molecular weights of 60 kD and 110 kD with the smaller protein approximately 4 fold more abundant.

The resulting partially purified PLA$_2$ enzyme preparation in Fractions 36–42 was examined for activity in the mixed micelle assay, described below. The specific activity of this preparation was found to be approximately 4 μmols/min/mg.

Fraction 39 was rechromatographed on the G3000=SW size exclusion column using 0.25 mL fractions. The 60 kD protein ran as a dimer preceding the 110 kD protein. When the 110 kD fraction was removed from the gel and this purified enzyme material was examined in the mixed micelle assay, the specific activity was found to be approximately 20 μmols/min/mg.

The 60 kD band was found to be associated with no activity on the same assay.

EXAMPLE 2—PURIFICATION OF MURINE PLA$_2$

The murine monocytic cell line RAW 264.7 [ATCC TIB71] was selected as a potential source for murine intracellular PLA$_2$. Using a humidified incubator at 37° C. and 10% CO$_2$, approximately 10$^{10}$ RAW 264.7 cells were cultured in DME media supplemented with 10% fetal bovine serum, penicillin (100 units/mL), streptomycin (100 µg/mL) and glutamine (20 mM). The cells were harvested by centrifugation. The pelletted cells were twice washed in ice cold PBS.

The washed cells were suspended in HEPES (10 mM) lysis buffer at pH7.5 containing sucrose (0.34M), EDTA (1 mM), DTT (0.1 mM), glycerol (10%), ATP (1 mM), leupeptin (1 µg/mL) and freshly added PMSF (1 mM). The cells were lysed by N$_2$ cavitation at 600–700 psi and the lysate was centrifuged at 5,000 g×60 minutes. PLA$_2$ was purified from the supernatant.

The supernatant was diluted 3 fold with Tris HCl (20 mM) buffer at pH7.5 containing glycerol (10%) and DTT (5 mM) to give a protein concentration of 5 mg/mL, and then one third of this protein solution was loaded onto a Mono-Q HR 10/10 column equilibrated with the same buffer and eluted with a 360 mL 0–1M KCl linear gradient at a flow rate of 4 mL/minute while collecting 10 mL fractions. The PLA$_2$ activity eluted at approximately 400 mM salt. The remaining material was processed in an identical fashion in two additional runs.

The fractions containing activity were adjusted to 0.5M NH$_4$SO$_4$, centrifuged at 30,000g×20 minutes, and loaded onto a Biorad Phenyl-5 PW column (75 mm×7.5 mm) that was previously equilibrated with 20 mM Tris HCl buffer (pH7.5) containing 5 mM DTT and 0.5M NH$_4$SO$_4$. The PLA$_2$ activity was eluted at 1 mL/minute with a 15 mL reverse gradient from 0.5 to 0M NH$_4$SO$_4$ with an extended wash at 0M salt. The activity eluting at 0M salt was diluted 2.5 fold with potassium phosphate buffer (10 mM; pH6.8) containing CaCl2 (10 µM), DTT 5 mM) and glycerol (10%) and was loaded onto a Biogel HPHT column (7.8×100 mm) equilibrated with the same buffer.

Protein was eluted into fractions (1 mL) by a linear potassium phosphate gradient (10–500 mM) at a flow rate of 0.4 mL/minute. The activity eluted near 130 mM phosphate. The active fractions were concentrated in a Centricon-30 and injected onto a TSK-Gel G3000-SW size exclusion column (60 cm×7.5 mm) which was both equilibrated and eluted with pH6.5 MES buffer (40 mM) containing KCl (300 mM), DTT (5 mM) and octylglucoside (3 mM). The flow rate Was 0.4 mL/minute, and the fraction size was 0.25 mL/minute.

When this fraction of purified enzyme material was examined in the mixed micelle assay described below, the specific activity was found to be approximately 20 µmols/min/mg. The activity eluted at a molecular weight of approximately 100 kD. Fractions from the sizing column were analyzed by SDS-PAGE using Biorad silver stain for visualization to confirm the purity of the preparation. The activity correlated with a 100 kD band.

EXAMPLE 3—ASSAYS FOR PLA$_2$ ENZYME ACTIVITY

A Mixed Micelle Assay

The currently preferred method of assay for PLA$_2$ activity is the mixed micelle assay using 1-palmitoyl 2-[1-$^{14}$C] arachidonoyl phosphatidylcholine as substrate and Triton as the micelle forming detergent. This assay is performed as follows:

1-Palmitoyl 2-[1-$^{14}$C] arachidonoyl phosphatidylcholine (50 nmol; 200,000 dpm) is dried under nitrogen and then resuspended in 0.5 mL glycine buffer (80 mM) at pH9.0 containing Triton (200 µM), CaCl$_2$ (5 mM), fatty acid free bovine serum albumin (250 µg/mL) and glycerol (70%). The suspension is sonicated to form mixed micelles of phospholipid and Triton.

Aliquots of PLA$_2$ protein solution to be assayed are added to the mixed micelle solution and incubated at 37° C. in a shaking water bath. After a defined time period, the reaction is quenched by the addition of 2.5 mL of isopropanol, heptane, and 0.5 M H$_2$SO: (800:200:40) with brief vortexing. Heptane (1.5 mL) and water (1.0 mL) are added and the solution is vortexed for 10 seconds.

The solution separates into an upper phase of heptane, which contains the [1-$^{14}$C] arachidonic acid liberated by PLA$_2$, plus a small fraction of unreacted substrate, and a lower isopropanol/aqueous phase which contains the bulk of the unreacted substrate. One milliliter of the heptane phase is loaded on a silica column (200 mg) and eluted by ethyl ether (1 mL). The fatty acid is eluted while the phosphatidyl choline is retained. The eluate is mixed with scintillant and the radioactivity measured.

This assay may be performed using various concentrations of the components, alternative phospholipids, different detergents or divalent metals, and a range of pH.

B. Liposome Assay

For the performance of a liposome assay, the same procedure as described for the micelle assay is performed, except detergent is not used. In this case, the phospholipid forms a liposome, instead of a mixed micelle. All the variations mentioned above may increase the sensitivity of the enzyme to inhibitors. This form of the assay may also be employed to detect activity of compounds to inhibit PLA$_2$.

C. Natural Cell Membrane Assay

As an alternative source of substrate, natural cell membranes may be isolated, and freed of endogenous PLA$_2$ by EDTA extraction or repeated freeze-thaw cycles. The membranes are then added to exogenous PLA$_2$. The free fatty acids resulting from the PLA$_2$ activity may be detected by gas chromatography.

EXAMPLE 4—PROTEIN SEQUENCE ANALYSIS OF HUMAN PLA$_2$

Human PLA$_2$ from fractions 39 and 40 from the Mono-Q HR 5/5 column and the active fractions from the second sizing column in Example 1 were combined and run on a 7.5% SDS-PAGE gel. As a reference, a small aliquot of the sample was iodinated with $^{125}$I and run out on the gel with the rest of the sample. The region of the gel corresponding to molecular weight 110 kD, as determined by autoradiography, was excised and digested by catalytic amounts of trypsin (2% w/w).

The resulting tryptic peptides were separated by reverse-phase chromatography on a Vydac C-4 column using a linear gradient of acetonitrile on 0.1% trifluoroacetic acid at 1% acetonitrile per minute. Eluted proteins were monitored by UV absorbance at 214 and 280 nm.

Several peptides were subjected to automated gas phase microsequencing:

(1) G S T M E E E L E N I T T K
(2) I Y E P L D V
(3) M N K
(4) I D P Y V F D
(5) K Y K A p G V P
(6) E A M V E S I E Y

Active fractions from the RAW 264.7 PLA$_2$ material purified as in Example 2 were sequenced in an analogous fashion.

EXAMPLE 5—cDNA LIBRARY CONSTRUCTION AND SCREENING cDNA libraries are synthesized from polyadenylated RNA from the human U937 genomic cell line and the RAW 264.7 cell lines, respectively, and cloned into lambda ZAP [Stratagene Cloning Systems, La Jolla, Calif.] essentially as described in J. J. Toole et al, *Nature*, 312:342-347 (1984)] with the following exceptions: the adapters used to blunt-end ligate to the double-stranded cDNA have the sequence 5' CTCTAGAGT-CCACGG 3' and 3' GAGATCTCAGCTGCCTTAA 5'.

For probing the human cDNA, a portion of the tryptic peptide (1) above (amino acid sequence M E E E L E) was used to design a pool of 48-fold degenerate oligonucleotides of 17 bases. An overlapping portion of tryptic (1) above (amino acid sequence E L E N I T) was also used to design a 140-fold degenerate anti-sense oligonucleotide. The tryptic peptide (5) above (amino acid sequence K Y K A P G) was used to design a 96-fold oligonucleotide. The synthetic pools contained all possible coding sequences for the listed peptides, and were used to screen 300,000 recombinant bacteriophage by the method of K. Jacobs et al, *Nature*, 313:806-810 (1985).

One human clone, designated clone 38, was shown to hybridize with all three oligonucleotides. Clone 38 was a partial clone, lacking the coding region for the amino-terminal 292 amino acids. THis partial clone was used to screen 1,200,000 recombinant bacteriophage using the protocol described in M. Katan et al, *Cell*, 54:171-177 (1988). Two bacteriophage, clones 1 and 19 contained approximately 3 kb cDNA inserts which were of sufficient length to encode a 110 kD protein. The sequence for both cones were determined for both strands using a Bal31 nuclease deletion series protocol [Poncz et al., *Proc. Nat. Acad. Sci USA*, 79:4298-4302 (1982)] with subsequent subcloning into appropriate M13 vectors [Messing and Viera, *Gene*, 19:269-276 (1982)] followed by sequence determination as described by Sanger et al, *Proc. Natl. Acad. Sci. USA*, 74:5463-5467 (1977). This analysis indicated that clone 19 encodes a protein of 85,000 daltons molecular weight that contains all of the tryptic peptides identified by protein sequencing. Clone 1 was identical in the coding region to clone 19 with the exception of a one base deletion.

Clone 19 is the source of the DNA and predicted amino acid sequence of Table I above.

EXAMPLE 6—PREPARATION OF RECOMBINANT mPLA$_2$

Essentially the same procedures described above were employed to recombinant murine PLA$_2$. A sequence from clone 19 of Table I (from base #877 to the 3' end of the sequence of Table I) was used to screen the RAW 264.7 cDNA library. Clone 7, which was isolated from a library of 1×10$^6$ clones, was partially sequenced as shown in Table II.

The purified RAW 264.7 PLA$_2$ was digested into tryptic fragments and sequenced as described for the human PLA$_2$ enzyme. The sequence of two tryptic fragments were obtained: (6) G T F G D M L D T P D P Y V E and (7) E N E E A E K E Y Q S D N Q A. The sequence for tryptic (7) disagreed at two amino acids within the deduced sequence. Based on the partial sequence, the RAW 264.7 enzyme is the murine homologue of the human PLA$_2$ of this invention.

Further sequences are selected from this clone to rescreen the library to obtain the entire coding region for muPLA$_2$.

EXAMPLE 7—EXPRESSION OF hPLA$_2$ IN COS CELLS

To obtain recombinant expression of the hPLA$_2$ of this invention in COS-1 cells, clone 19 from Example 5 above in bluescript was excised by Sal I digestion, and bluescript was digested with PvuI to enable agarose gel separation of the 3 kb insert from the 3 kb bluescript. The expression plasmid PLA$_2$-PMT2 was constructed by inserting the excised cDNA encoding PLA$_2$ into a SalI site that was engineered into the EcoRI site of the COS expression vector, PMT-2, a beta lactamase derivative of p91023 [Wong et al, *Science*, 228:810-815 (1985)]. The plasmid was then transfected into 2×10$^6$ COS cells in a 10 cm dish by the DEAE dextran protocol [L. M. Sompayrac et al., *Proc. Natl. Acad. Sci. USA*, 78:7575 (1981)] with the addition of a chloroquine treatment [H. Luthman et al, *Nucl. Acids Res.*, 11:1295 (1983)]. The cells are grown in conventional media and the conditioned medium from the transfected COS cells contains PLA$_2$ enzymatic activity as measured in the mixed micelle assay of Example 3. Generally cells were harvested 60 hours after the addition of the DNA.

The expression of PLA$_2$ activity in cells transfected with the PLA$_2$-PMT2 vector was 140-fold greater than in cells transfected with the vector alone, as determined by the mixed micelle assay.

EXAMPLE 8—INSECT CELL EXPRESSION

To create an insect cell expression system for PLA$_2$ of the invention, the cDNA sequence of Table I flanked by EcoRI linkers (New Engl. Biolab) is inserted into a polyhedrosis virus expression vector, designated pEV/55. pEV/55 may be obtained by removing the CSF sequence from the plasmid pEV55-CSF+ harbored in *E. coli* strain JM101 on deposit at the ATCC under No. 40240, by digesting that plasmid with EcoRI. This plasmid is described in D. Miller et al, supra, and contains approximately 3.5 kb of viral DNA from the EcoRI fragment of the L-1 variant of the Autographa californica nuclear polyhedrosis virus and a polylinker sequence containing the following endonuclease restriction sites: Bgl II, XhoI, EcoRI, XbaI, OlaI and KpnI. To allow insertion of the EcoRI fragment of PLA$_2$/cDNA, pEV/55 is digested with EcoRI and the PLA₂/cDNA ligated therein. The selected plasmid is designated pEV55-PLA₂. Transformation of *E. coli* strain JM101 with pEV55-PLA₂ is followed by analysis of some of the recovered plasmids, both for insertion of the PLA₂ gene and for proper orientation of the insert.

pEV55-PLA₂ is introduced into the insect virus chromosome by co-transfection With Wild-type AcNPV DNA into *Spodoptera frugiperda* IPLB-SF21 cell line [J. L. Vaughn et al, In Vitro, 13:213–217 (1977)]. Purified *Autographa californica* NPV DNA and pEV55-PLA₂ DNA are introduced into *Spodoptera frugiperda* cells growing on tissue culture dishes by a calcium phosphate transfection procedure [K. N. Potter and L. K. Miller, *J. Invertebr. Path.*, 36:431–432 (1980)]. The joint introduction of these DNAs into the cells results in a recombination between pEV55-PLA₂ and the viral DNA at the regions of homology between the two; that is, the polyhedrin gene region. Progeny virus from a double recombination event lose the polyhedrin gene and contain the PLA₂ gene under operative control of the polyhedrin promoter.

The progeny virus present in the media over the transfected cells are plaqued onto a fresh monolayer of cells at several different dilutions. The resulting plaques are visually scored and the recombinant virus selected based on the PIB-minus phenotype. A virus which has lost its polyhedrin gene, as would a virus containing a PLA₂ cDNA inserted at the polyhedrin encoding locus, will not produce polyhedrin inclusion bodies (PIBs). Plaques that appear PIB-deficient are selected, excised and amplified on fresh cells. The supernatant over these cells is assayed for PLA₂ activity.

The cell and viral manipulations are performed according to G. D. Pennock et al, *Mol. Cell. Biol.*, 4:399–406 (March 1984). However, those of ordinary skill in the art to which this invention pertains will appreciate that other viruses, strains, host cells, promoters and vectors containing the cDNA encoding the amino acid sequence of Table I may also be used in the practice of this invention. The DNA manipulations employed in the examples are, unless specifically set forth herein, in accordance with Maniatis et al, cited above.

EXAMPLE 9—EXPRESSION OF PLA2 IN BACTERIA

To produce PLA₂ in bacteria, the cDNA encoding it is transferred into an appropriate expression vector, of which numerous types are known in the art for bacterial expression, using standard molecular biology techniques. One skilled in the art can manipulate the sequences encoding PLA₂ by eliminating any mammalian regulatory sequences flanking the coding sequences and inserting bacterial regulatory sequences to create bacterial vectors for expression of PLA₂ by bacterial cells. The cDNA encoding PLA₂ may be further modified to contain different codons to optimize bacterial expression, as is known in the art.

For example, clone 19 described above in Example 5 in bluescript is excised by digestion with HgiAI and NsiI to provide a 2.6 kb fragment encoding PLA₂ of Table I, starting at base 41 and extending 350 base paris into the 3' untranslated region. This fragment is ligated at the HgiAI site to the following synthetic duplex:

5' TATGTOTTTTATOGATcOTTATcAACATAT-TATCGTTGAGCA

3'    ATACAGAAAATAGCTAGGAATAGTT-GTATAATAGCAACTCGT

The 2.6 kb fragment plus the synthetic duplex are then ligated into pAL-981 [ATCC 40134], which is previously digested with NdeI and PstI to give pAL-PLA₂-981. This plasmid also contains the amp resistance gene, an aspA terminator, an origin of replication site, the bacteriophage T7 ribosome binding site and the bacteriophage lambda pL promoter and bacteriophage lambda transcription terminator.

Plasmid pALPLA₂-981 is then transformed by conventional techniques into a suitable bacterial host cell, e.g., an *E. coli* strain, which contains appropriate elements for controlling the PL promoter for expression of the PLA₂ protein. Other bacterial expression systems, such as disclosed in Y. Emori et al, *J. Biol. Chem.*, 264:21885–21890 (1989), may also be constructed for expression of PLA₂ of this invention.

Bacterially produced PLA₂ is predicted to have a specific activity in the mixed micelle assay of about approximately 20 μmols/min/mg protein.

EXAMPLE 10—CONSTRUCTION OF CHO CELL LINES EXPRESSING HIGH LEVELS OF PLA₂

One method for producing high levels of the PLA₂ protein of the invention from mammalian cells involves the construction of cells containing multiple copies of the cDNA encoding PLA₂.

The cDNA contains an amplifiable marker, e.g., the DHFR gene for Which cells containing increasing concentrations of methotrexate (MTX) according to the procedures of Kaufman and Sharp, *J. Mol. Biol.*, (1982) supra. This approach can be employed with a number of different cell types.

For example, the vector PLA₂-PMT2 containing the PLA₂ gene in operative association with other plasmid sequences enabling expression thereof in COS cells, and described and deposited above, contains the PLA₂ coding region and the DHFR coding region on a single plasmid.

Alternatively, the pALPLA₂-981 vector described above for bacterial expression may be employed for co-transfection with a separate plasmid bearing the DHFR gene, such as pAdD26SVpA3 [Kaufman, *Proc. Natl. Acad. Sci. USA*, 82:689–693 (1985)].

Either the single plasmid bearing both genes or two separate plasmids are introduced into DHFR-deficient CHO cells, DUKX-BII by calcium phosphate coprecipitation and transfection. DHFR expressing transformants are selected for growth in alpha media with dialyzed fetal calf serum. Transformants are checked for expression of PLA₂ by bioassay, immunoassay or RNA blotting and positive pools are subsequently selected for amplification by growth in increasing concentrations of MTX (sequential steps in 0.02, 0.2, 1.0 and 5 uM MTX) as described in Kaufman et al., *Mol. Cell Biol.*, 5:1750 (1983). The amplified lines are cloned, and PLA₂ protein expression is monitored by the mixed micelle assay. PLA₂ expression is expected to increase with increasing levels of MTX resistance.

In any of the expression systems described above, the resulting cell lines can be further amplified by appropriate drug selection, resulting cell lines recloned and the level of expression assessed using the mixed micelle assay described in Example 3.

EXAMPLE 11—SCREENING METHOD FOR COMPOUNDS THAT INHIBIT PLA$_2$ ENZYME ACTIVITY

An exemplary screening technique is described which enables selection of chemical or pharmaceutical agents having the ability to inhibit PLA$_2$ activity, which employs the PLA$_2$ enzymes of the present invention. Such compounds thereby indicate potential use in controlling the inflammatory response.

For example, the PLA$_2$ enzyme of Example 5 and a selected compound to be screen are added to liposomes, mixed micelles, or natural membranes devoid of endogenous PLA$_2$ activity, in the assays described in Example 3. If the compound is found to inhibit the PLA$_2$ activity, i.e., render the enzyme incapable of cleaving the phospholipid substrate, it has potential anti-inflammatory activity.

Inhibitors may compete with substrate for the enzyme active site or they may bind to an allosteric site. Alternatively, the compound may bind to the phospholipid, or in the case of the natural membranes, a non-phospholipid component of the membrane, and thereby either prevent the enzyme from binding or alter the membrane structure in a fashion that blocks catalysis. By application of selective labelling of components of the assays, e.g., the arachidonic acid, the inhibitory capacity of each selected compound may be measured for further use as an anti-inflammatory agent.

Numerous modifications and variations of the present invention are included in the above-identified specification and are expected to be obvious to one of skill in the art. For example, other screening techniques may be employed to determine the ability of selected compounds to inhibit PLA$_2$ activity. Such modifications and alterations to the compositions and processes of the present invention are believed to be encompassed in the scope of the claims appended hereto.

What is claimed is:

1. A cDNA encoding a human phospholipase A$_2$ enzyme having the amino acid sequence set forth in Table I, said DNA sequence being selected from the group consisting of
   i) a cDNA having the DNA sequence set forth in Table I;
   ii) a cDNA comprising the SalI insert in plasmid PMT-PLA$_2$ having accession number ATCC 40759; and
   iii) a cDNA which hybridizes to the cDNA of i) or ii) under stringent conditions and which encodes said enzyme.

2. The cDNA of claim 1, comprises the DNA sequence set forth in Table I.

3. The cDNA of claim 1, comprises the SalI insert in plasmid PMT-PLA$_2$ having accession number ATCC 40759.

4. The cDNA of claim 1, comprises a cDNA which hybridizes to a cDNA having the DNA sequence set forth in Table I under stringent conditions and which encodes said enzyme.

5. A cDNA encoding a murine phospholipase A$_2$ enzyme having a partial amino acid sequence as set forth in Table II, said cDNA being characterized by containing the DNA sequence set forth in Table II.

6. An expression vector containing a cDNA selected from the group consisting of the cDNAs of any one of claims 1, 2, 3, 4 and 5, said cDNA being in operative association with a regulatory sequence capable of directing the replication and expression of said cDNA in a host cell.

7. The vector of claim 6, wherein the cDNA is the cDNA comprising the SalI insert in plasmid PMT-PLA$_2$ having accession number ATCC 40759.

8. A cell selected from the group consisting of a mammalian cell, an insect cell, and a bacterial cell, said cell being transformed with the expression vector of claim 6.

9. The cell of claim 8, wherein the cell is a mammalian cell and the expression vector contains the cDNA comprising the SalI insert in plasmid PMT-PLA$_2$ having accession number ATCC 40759.

10. A process for producing a phospholipase A$_2$ enzyme having the amino acid sequence set forth in Table I, which comprises culturing a host cell transformed with a cDNA having the DNA sequence set forth in Table I, said cDNA being in operative association with a regulatory sequence capable of directing the replication and expression of said cDNA in said cell such that said enzyme is produced and isolated from culture.

11. A process for producing a phospholipase A$_2$ enzyme having a partial amino acid sequence as set forth in Table II, which comprises culturing a host cell transformed with a cDNA characterized by containing the DNA sequence set forth in Table II, said cDNA being in operative association with a regulatory sequence capable of directing the replication and expression of said cDNA in said cell such that said enzyme is produced and isolated from culture.

* * * * *